United States Patent [19]

Schuetz et al.

[11] Patent Number: 4,957,937

[45] Date of Patent: Sep. 18, 1990

[54] SUBSTITUTED N-HYDROXYPYRAZOLES AND FUNGICIDES WHICH CONTAIN THESE COMPOUNDS

[75] Inventors: Franz Schuetz, Ludwigshafen; Hubert Sauter, Mannheim; Siegbert Brand, Weinheim; Bernd Wenderoth, Lampertheim; Ulf Baus, Dossenheim; Wolfgang Reuther, Heidelberg; Gisela Lorenz, Neustadt; Eberhard Ammermann, Ludwigshafen, all of Fed. Rep. of Germany

[73] Assignee: BASF Aktiengesellschaft, Ludwigshafen, Fed. Rep. of Germany

[21] Appl. No.: 478,963

[22] Filed: Feb. 12, 1990

[30] Foreign Application Priority Data

Feb. 25, 1989 [DE] Fed. Rep. of Germany ....... 3905948

[51] Int. Cl.$^5$ .................. A01N 43/56; C07D 231/12; C07D 231/54; C07D 231/56
[52] U.S. Cl. .................................. 514/407; 548/369; 548/372; 548/375; 548/376; 548/377
[58] Field of Search .............. 548/369, 372, 375, 376, 548/377; 514/407

[56] References Cited

U.S. PATENT DOCUMENTS 4,764,527 8/1988 Wagner et al. .................... 548/375

*Primary Examiner*—Robert W. Ramsuer
*Attorney, Agent, or Firm*—Oblon, Spivak, McClelland, Maier & Neustadt

[57] ABSTRACT

Substituted N-hydroxypyrazoles of the general formula

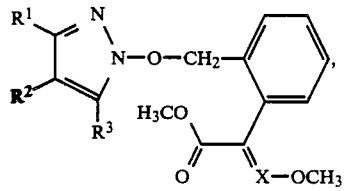

where
$R^1$, $R^2$ and $R^3$ are identical or different and are hydrogen, alkyl, haloalkyl, cycloalkyl, alkoxycarbonyl, halogen, aryl or arylalkyl, the aromatic ring being unsubstituted or substituted,
or $R^2$ and $R^3$ form, with the pyrazole ring, a substituted or unsubstituted aromatic or aliphatic ring,
X is CH or N, and their plant-tolerated acid addition salts and metal complexes,
and fungicides containing these compounds.

8 Claims, No Drawings

SUBSTITUTED N-HYDROXYPYRAZOLES AND FUNGICIDES WHICH CONTAIN THESE COMPOUNDS

The present invention relates to novel substituted N-hydroxypyrazoles and fungicides which contain these compounds.

The use of substituted methyl acrylates, e.g. methyl α-(2-phenoxymethylphenyl)-β-methoxyacrylate, as fungicides has been disclosed (DE 35 45 319). However, its fungicidal action is unsatisfactory.

We have now found that substituted N-hydroxypyrazoles of the general formula I

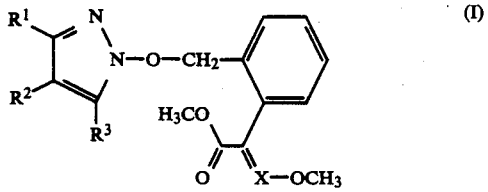

where $R^1$, $R^2$ and $R^3$ are identical or different and are hydrogen, $C_1$-$C_4$-alkyl, $C_1$-$C_2$-haloalkyl, $C_3$-$C_6$-cycloalkyl, are $C_1$-$C_4$-alkoxycarbonyl, halogen, aryl or aryl-$C_1$-$C_4$-alkyl, it being possible for the aromatic ring to be substituted by one or more of the following: $C_1$-$C_4$-alkyl, $C_3$-$C_6$-cycloalkyl, $C_1$-$C_2$-haloalkyl, $C_1$-$C_4$-alkoxy, halogen, cyano or nitro, or $R^2$ and $R^3$ form, with the pyrazole ring, an aromatic or aliphatic ring which can be substituted by $C_1$-$C_4$-alkyl, X is CH or N, and the acid addition salts and metal complexes thereof which are tolerated by plants, have an excellent fungicidal action which is better than that of the known substituted methyl acrylates.

Examples of possible meanings of the radicals listed for the general formula are the following:

$R^1$, $R^2$ and $R^3$ are identical or different and are $C_1$-$C_4$-alkyl (e.g. methyl, ethyl, n- or iso-propyl, n-, iso-, sec- or tert-butyl), $C_1$-$C_2$-haloalkyl (e.g. difluoromethyl, trifluoromethyl, chloromethyl, dichloromethyl, trichloromethyl or pentafluoroethyl), $C_3$-$C_6$-cycloalkyl (e.g. cyclopropyl, cyclobutyl, cyclopentyl or cyclohexyl), $C_1$-$C_4$-alkoxycarbonyl (e.g. methoxycarbonyl, ethoxycarbonyl, propoxycarbonyl, butoxycarbonyl), halogen (e.g. fluorine, chlorine, bromine or iodine) or aryl (e.g. phenyl) or aryl-$C_1$-$C_4$-alkyl (e.g. benzyl, 2-phenylethyl, 3-phenylpropyl or 4-phenylbutyl), it being possible for the aromatic ring to substituted by one or more (one to three) of the following: $C_1$-$C_4$-alkyl (e.g. methyl, ethyl, propyl or butyl), $C_3$-$C_6$-cycloalkyl (e.g. cyclopropyl, cyclobutyl, cyclopentyl or cyclohexyl), $C_1$-$C_2$-haloalkyl (e.g. trifluoromethyl), $C_1$-$C_4$-alkoxy (e.g. methoxy, ethoxy, n- or iso-propoxy, n-, iso-, sec- or tert-butoxy), halogen (e.g. fluorine, chlorine, bromine or iodine), cyano or nitro or $R^2$ and $R^3$ form, together with the pyrazole ring, an aromatic or aliphatic ring (e.g. indazole or tetrahydroindazole) which can be substituted (one to three times) by $C_1$-$C_4$-alkyl (e.g. methyl, ethyl, n- or iso-propyl, n-, iso-, sec- or tert-butyl), and X is CH or N.

Examples of salts are the acid addition salts which are tolerated by plants, e.g. the salts with inorganic or organic acids such as the salts of hydrochloric acid, hydrobromic acid, nitric acid, oxalic acid, acetic acid, sulfuric acid, phosphoric acid or dodecylbenzenesulfonic acid. The activity of the salts derives from the cation, so that the choice of the anion is generally arbitrary.

It is also possible to convert the compounds of the formula I into metal complexes by conventional methods. This can take place by reacting these compounds with metal salts, e.g. salts of copper, zinc, iron, manganese or nickel, for example copper(II) chloride, zinc(II) chloride, iron(III) chloride, copper(II) nitrate, manganese(II) chloride or nickel(II) bromide.

The preparation of the novel compounds of the general formula (I) may, because of the C=C or C=N double bond, result in mixtures of E and Z isomers. The latter can be separated in a conventional manner, e.g. by crystallization or chromatography, into the individual components. The invention relates both to the individual isomeric compounds and to the mixtures thereof, and all of them can be used as fungicides.

The novel compounds of the general formula (I) as claimed in claim 1 are prepared, for example, in such a way that the N-hydroxypyrazoles of the general formula (II) are first converted with a base (e.g. sodium hydroxide or potassium hydroxide) into the corresponding sodium or potassium salts, and the latter are then reacted in an inert solvent or diluent with a substituted benzyl compound of the general formula III.

Examples of suitable solvents or diluents are acetone, acetonitrile, dimethyl sulfoxide, dioxane, dimethylformamide, N-methylpyrrolidone, N,N'-dimethylpropyleneurea or pyridine. It may also be advantageous to add to the reaction mixture a catalyst such as tetramethylethylenediamine or tris(3,6-dioxoheptyl)amine in an amount of from 0.01 to 10% by weight based on compound III.

The reactions can also be carried out in a two-phase system (e.g. carbon tetrachloride/water). Examples of suitable phase-transfer catalysts are trioctylpropylammonium chloride or cetyltrimethylammonium chloride.

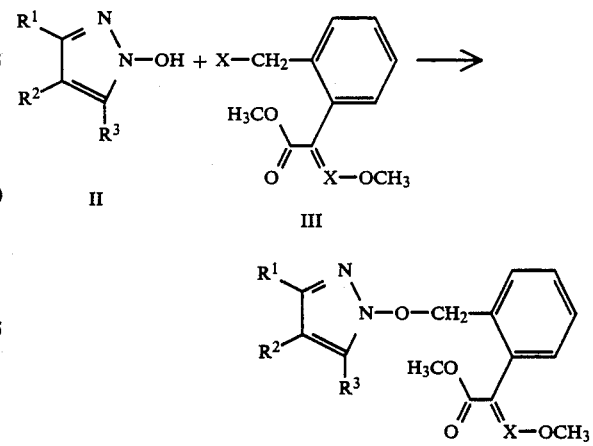

$R^1$, $R^2$, $R^3$ and X have the abovementioned meanings, and Y is chloride, bromide, p-toluenesulfonate, methanesulfonate or trifluoromethanesulfonate.

To prepare the N-hydroxypyrazoles of the formula II required as starting compounds, pyrazoles of the general formula IV are first converted in a conventional manner, using an alkali metal hydroxide, hydride or carbonate, into the metal salts thereof of the general formula V (Me+ is a cation of the alkali metal). The resulting metal salts of the formula V are then reacted in an inert organic solvent (e.g. tetrahydrofuran) or in a two-phase system (e.g. toluene/water) in the presence or absence of a phase-transfer catalyst (e.g. benzyltriethylammonium chloride) with dibenzoyl peroxide. The reaction is carried out at from 0° to 60° C.

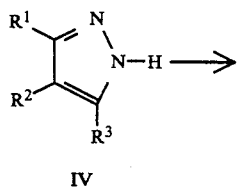

IV

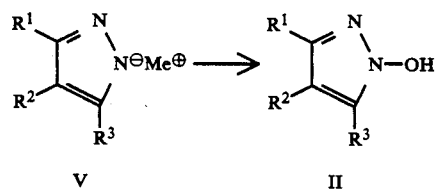

V          II

An alternative procedure is to react an alkali metal salt of the general formula V with an aliphatic or aromatic peroxycarboxylic acid in such a way that the reaction takes place at from −5° C. to 60° C. The reaction can be carried out in water as solvent or in a two-phase system composed of water and an inert organic solvent which is immiscible with water (e.g. toluene), in the presence of absence of a suitable phase-transfer catalyst (e.g. benzyltriethylammonium chloride). The peroxycarboxylic acid can be prepared before the reaction from $H_2O_2$ and a carbonyl halide or carboxylic anhydride in the reaction mixture, or can be employed in the form of an alkali metal or alkaline earth metal salt.

Also required for the preparation of the novel compounds of the general formula I are the substituted benzyl compounds of the general formula III. Compounds of the general formula IIIa (X=N, Y=chloride or bromide) are obtained by halogenation of methyl 2-methylphenylglyoxylate O-methyloxime VI by literature methods. This is achieved, for example, with bromine or chlorine in an inert solvent (e.g. tetrachloromethane), with or without irradiation (e.g. from an Hg vapor lamp, 300 W), or by reaction with N-chloro- or N-bromosuccinimide (cf. Horner, Winkelmann, Angew. Chem 71 (1959) 349).

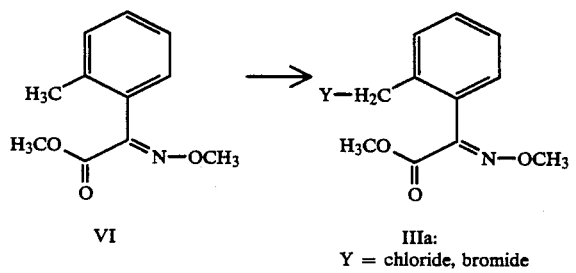

VI          IIIa:
                          Y = chloride, bromide

Methyl 2-methylphenylglyoxylate O-methyloxime VI can be prepared by reacting methyl 2-methylphenylglyoxylate VII with, for example, (a) O-methylhydroxylamine hydrochloride or (b) hydroxylamine hydrochloride to give the corresponding oxime and then reacting the latter with a methylating agent of the formula $CH_3$-L where L is a leaving group (e.g. chloride, bromide, iodide or methylsulfate) (cf. DE 36 23 921).

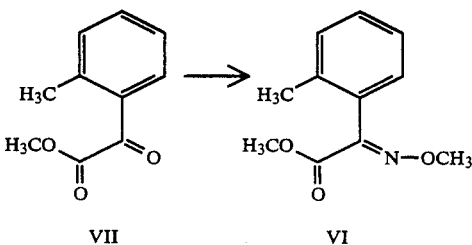

VII          VI

Benzyl halides of the general formula IIIa (X=N, Y=chloride or bromide) are also obtained when methyl 2-halomethylphenylglyoxylates of the formula VIII (Hal=chloride or bromide) are reacted (a) with O-methylhydroxylamine hydrochloride or (b) with hydroxylamine hydrochloride to give the corresponding oxime and then reacting the latter with a methylating agent of the formula $CH_3$-L where L is a leaving group (e.g. chloride, bromide, iodide or methylsulfate) (cf. DE 36 23 921).

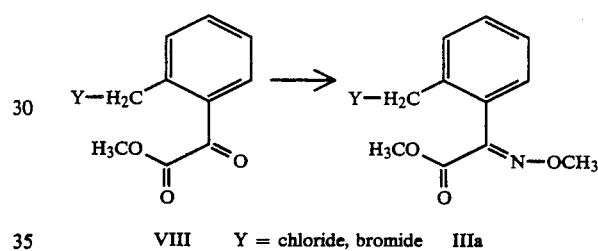

VIII    Y = chloride, bromide    IIIa

Methyl 2-halomethylphenylglyoxylates of the formula VIII (Hal=chloride or bromide) can be prepared by halogenating methyl 2-methylphenylglyoxylates VII by literature methods. The reaction is carried out, for example, with bromine or chlorine in an inert solvent (e.g. tetrachloromethane) with or without irradiation (e.g. from an Hg vapor lamp, 300 W) or with N-chloro- or N-bromosuccinimide (cf. Horner, Winkelmann, Angew. Chem. 71 (1959) 349).

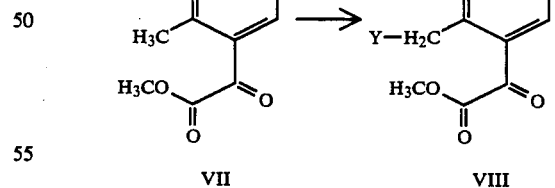

VII          VIII

Substituted benzyl compounds of the general formula IIb (X=CH, Y=chloride or bromide) are known or can be prepared by known processes. Appropriate preparation processes are described, for example, in DE 35 19 280, DE 35 45 318 and DE 35 45 319.

Substituted benzyl compounds of the general formula IIIc (X=CH or N, Y=p-toluenesulfonate, methanesulfonate or trifluoromethanesulfonate) can be prepared from the corresponding compounds of the general formula IIIa (X=N, Y=chloride or bromide) or IIIb (X=CH, Y=chloride or bromide) by reaction with p-toluenesulfonic acid (Y=p-toluenesulfonate), methanesulfonic acid (Y=methanesulfonate) or trifluoromethanesulfonic acid (Y=trifluoromethanesulfonate). The reactions can be carried out, for example, in an inert solvent or diluent (e.g. dimethylformamide) in the presence of a base (e.g. potassium carbonate). An alternative procedure is to convert the appropriate sulfonic acid into its sodium or potassium salt and then to react the latter in an inert solvent or diluent (e.g. dimethylformamide) with a compound of the general formula IIIa or IIIb to give the substituted benzyl compounds of the general formula IIIc.

EXAMPLES

The examples and procedures which follow are intended to illustrate the preparation of the novel active substances and their precursors.

PROCEDURE 1

Methyl 2-bromomethylphenylglyoxylate O-methyloxime 21.4 g (0.133 mol) of bromine are added to a stirred solution of 27.5 g (0.133 mol) of methyl 2-methylphenylglyoxylate O-methyloxime in 400 ml of tetrachloromethane. The mixture is then refluxed while irradiating with a 300 W Hg vapor lamp for four hours. It is then concentrated, the residue is taken up in ethyl acetate/water, and the organic phase is washed with $H_2O$, dried over sodium sulfate and concentrated. The crude product is purified by chromatography on silica gel with cyclohexane/ethyl acetate (9/1). 17.4 g (46%) of the abovementioned compound are obtained as an oil.

EXAMPLE 1

Methyl 2-(3,5-dimethyl-1-pyrazolyloxymethyl)phenylglyoxylate O-methyloxime (compound no. 28)

(a) 28.8 g (0.30 mol) of 3,5-dimethylpyrazole are dissolved in 500 ml of tetrahydrofuran and, at room temperature, 9.0 g (0.30 mol) of an 80% suspension of sodium hydride in liquid paraffin are added a little at a time. After the evolution of hydrogen has ceased, the mixture is cooled to 5° C. and 24.2 g (0.1 mol) of dry dibenzoyl peroxide dissolved in 500 ml of tetrahydrofuran are added in such a way that the temperature of the reaction mixture does not exceed 25° C. After the addition is complete, the reaction mixture is stirred for 10 minutes and then ice-water and petroleum ether are added and shaken. The aqueous phase is separated off and acidified with sulfuric acid. It is extracted several times with cyclohexane and then with ethyl acetate. The combined ethyl acetate phases are dried over sodium sulfate and concentrated. This results in 8.4 g (25%) of 3,5-dimethyl-1-hydroxypyrazole (melting point 155° C.).

(b) 2.2 g (0.02 mol) of 3,5-dimethyl-1-hydroxypyrazole in 30 ml of ethanol are added dropwise to a solution of 1.2 g (0.02 mol) of potassium hydroxide in 50 ml of ethanol. The reaction mixture is stirred at room temperature for two hours and then concentrated. The residue is taken up in 60 ml of dimethylformamide, and 5.7 g (0.02 mol) of methyl 2-bromomethylphenylglyoxylate O-methyloxime in 30 ml of dimethylformamide are added. The mixture is stirred at 100° C. for two hours, the solvent is removed under reduced pressure, and the residue is taken up in methyl tert-butyl ether. The organic phase is washed with water, dried and concentrated. 3.7 g (59%) of the title compound are obtained as an oil (compound no. 28).

EXAMPLE 2

Methyl α-[2-(4-chloro-1-pyrazolyloxymethyl)phenyl]-β-methoxyacrylate (compound no. 9)

(a) 4.1 g (0.04 mol) of 4-chloropyrazole are dissolved in 16.8 g (0.15 mol) of a 50% strength KOH solution. The solution is cooled to 0° C. while stirring, and 3.4 g (0.05 mol) of a 50% strength aqueous solution of hydrogen peroxide are slowly added. Then 7.4 g (0.05 mol) of phthalic anhydride are added a little at a time, and the reaction mixture is subsequently warmed to 20° C. It is then stirred for several hours, briefly heated to 80° C. to decompose the peroxide and cooled again to room temperature (20° C.). The mixture is then acidified with sulfuric acid, filtered to remove the precipitated potassium sulfate and extracted with ethyl acetate. The combined organic phases are dried and concentrated. Cyclohexane is added to the residue, which crystallizes. This results in 3.2 g (68%) of 4-chloro-1-hydroxypyrazole (melting point 125° C.).

(b) 2.4 g (0.02 mol) of 4-chloro-1-hydroxypyrazole in 30 ml of ethanol are added dropwise to a solution of 1.2 g (0.02 mol) of potassium hydroxide in 50 ml of ethanol. The reaction mixture is stirred at room temperature for two hours and then concentrated. The residue is taken up in 60 ml of dimethylformamide, and 5.7 g (0.02 mol) of methyl α-(2-bromomethylphenyl)-β-methoxyacrylate in 30 ml of dimethylformamide are added. The mixture is stirred at 100° C. for two hours, a solvent is removed under reduced pressure and the residue is taken up in methyl tertbutyl ether. The organic phase is washed with water, dried and concentrated. 5.0 g (77%) of the title compound are obtained as an oil (compound no. 9).

The following compounds are prepared in a corresponding manner.

TABLE 1

Compounds of the formula I

The configuration statement refers to the methyl β-methoxyacrylate group or to the methyl glyoxylate O-methyloxime group.

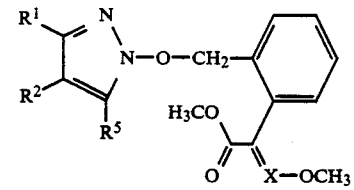

| No. | R$^1$ | R$^2$ | R$^3$ | X | mp. (°C.) |
|---|---|---|---|---|---|
| 1 | H | H | H | CH | oil (E) |
| 2 | H | H | H | N | oil (E) |
| 3 | H | CH$_3$ | H | CH | |
| 4 | H | CH$_3$ | H | N | |
| 5 | H | C$_2$H$_5$ | H | CH | |
| 6 | H | C$_2$H$_5$ | H | N | |
| 7 | H | F | H | CH | |
| 8 | H | F | H | N | |
| 9 | H | Cl | H | CH | oil (E) |
| 10 | H | Cl | H | N | oil (E) |
| 11 | H | Br | H | CH | |
| 12 | H | Br | H | N | |
| 13 | H | C$_6$H$_5$ | H | CH | |
| 14 | H | C$_6$H$_5$ | H | N | |

TABLE 1-continued

Compounds of the formula I

The configuration statement refers to the methyl β-methoxyacrylate group or to the methyl glyoxylate O-methyloxime group.

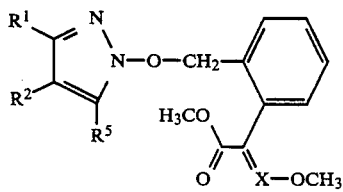

| No. | R¹ | R² | R³ | X | mp. (°C.) |
|---|---|---|---|---|---|
| 15 | H | 2-Cl—C₆H₄ | H | CH | |
| 16 | H | 2-Cl—C₆H₄ | H | N | |
| 17 | H | 4-Cl—C₆H₄ | H | CH | |
| 18 | H | 4-Cl—C₆H₄ | H | N | |
| 19 | H | 2-CH₃—C₆H₄ | H | CH | |
| 20 | H | 2-CH₃—C₆H₄ | H | N | |
| 21 | H | 4-CH₃—C₆H₄ | H | CH | |
| 22 | H | 4-CH₃—C₆H₄ | H | N | |
| 23 | H | C₆H₅—CH₂ | H | CN | |
| 24 | H | C₆H₅—CH₂ | H | N | |
| 25 | H | CO₂CH₃ | H | CH | |
| 26 | H | CO₂CH₃ | H | N | |
| 27 | CH₃ | H | CH₃ | CH | oil (E) |
| 28 | CH₃ | H | CH₃ | N | oil (E) |
| 29 | C₂H₅ | H | C₂H₅ | CH | |
| 30 | C₂H₅ | H | C₂H₅ | N | |
| 31 | F | H | F | CH | |
| 32 | F | H | F | N | |
| 33 | Cl | H | Cl | CH | |
| 34 | Cl | H | Cl | N | |
| 35 | Br | H | Br | CH | |
| 36 | Br | H | Br | N | |
| 37 | C₆H₅ | H | C₆H₅ | CH | |
| 38 | C₆H₅ | H | C₆H₅ | N | |
| 39 | C₆H₅—CH₂ | H | C₆H₅—CH₂ | CH | |
| 40 | C₆H₅—CH₂ | H | C₆H₅—CH₂ | N | |
| 41 | CH₃ | Cl | CH₃ | CH | |
| 42 | CH₃ | Cl | CH₃ | N | |
| 43 | CH₃ | Br | CH₃ | CH | |
| 44 | CH₃ | Br | CH₃ | N | |
| 45 | C₂H₅ | Cl | C₂H₅ | CH | |
| 46 | C₂H₅ | Cl | C₂H₅ | N | |
| 47 | C₂H₅ | Br | C₂H₅ | CH | |
| 48 | C₂H₅ | Br | C₂H₅ | N | |
| 49 | CH₃ | CO₂CH₃ | CH₃ | CH | |
| 50 | CH₃ | CO₂CH₃ | CH₃ | N | |
| 51 | H | A | A | CH | |
| 52 | H | A | A | N | |
| 53 | H | B | B | CH | |
| 54 | H | B | B | N | |

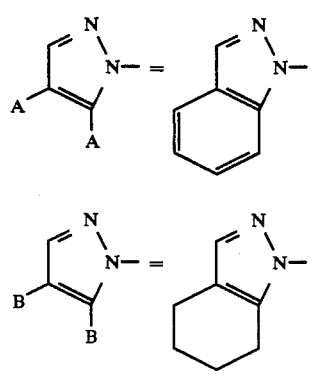

TABLE 2

Spectroscopic data (¹H-NMR and IR) of selected compounds from Table 1.

In the case of the NMR spectra, the chemical shift (δ) in ppm relative to tetramethylsilane is given. The solvent employed was CDCl₃.

In the case of the IR spectra, the wavelengths are given in cm⁻¹.

Compound no. 1

NMR:
3.67 (s, 3H); 3.73 (s, 3H); 5.17 (s, 2H); 5.96 (m, 1H); 6.96 (m, 1H); 7.16–7.37 (m, 5H); 7.60 (s, 1H).
IR (film):
1706, 1635, 1436, 1286, 1258, 1208, 1192, 1131, 1111, 748.

Compound no. 2

NMR:
3.87 (s, 3H); 4.04 (s, 3H); 5.13 (s, 2H); 5.98 (m, 1H); 7.00 (m, 1H); 7.17–7.45 (m, 5H).
IR (film):
1726, 1438, 1323, 1224, 1201, 1069, 1046, 1019, 963, 745.

Compound no. 9

NMR:
3.69 (s, 3H); 3.79 (s, 3H); 5.15 (s, 2H); 6.96 (s, 1H); 7.13–7.40 (m, 5H); 7.60 (s, 1H).
IR (film):
1706, 1636, 1286, 1258, 1209, 1191, 1131, 1111, 967, 770.

Compound no. 10

NMR:
3.88 (s, 3H); 4.04, (s, 3H); 5.13 (s, 2H); 7.01 (s, 1H); 7.16 (s, 1H); 7.20–7.49 (m, 4H).
IR (film):
1726, 1438, 1317, 1223, 1203, 1069, 1019, 982, 967, 768.

Compound no. 27

NMR:
1.89 (s, 3H); 2.20 (s, 3H); 3.68 (s, 3H); 3.73 (s, 3H); 5.13 (s, 2H); 5.63 (s, 1H); 7.13–7.39 (m, 4H); 7.60 (s, 1H).
IR (film):
1709, 1634, 1435, 1285, 1258, 1207, 1191, 1131, 1112, 770.

Compound no. 28

NMR:
1.88 (s, 3H); 2.20 (s, 3H); 3.83 (s, 3H); 4.02 (s, 3H); 5.08 (s, 2H); 5.63 (s, 1H); 7.20–7.43 (m, 4H).
IR (film):
1728, 1438, 1321, 1223, 1201, 1069, 1019, 959, 779, 770.

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
Rhizoctonia species in cotton and lawns,
Ustilago species in cereals and sugar cane,
*Venturia inaequalis* (Scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
Plasmopara viticola in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicidal agents generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, for example against Paecilomyces variotii.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 2 is mixed with 10 parts by weight of N-methyl-α-pyrrolidone. A mixture is obtained which is suitable for application in the form of very fine drops.

II. 20 parts by weight of compound no. 9 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 27 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 2 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 9 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 27 is intimately mixed with 97 parts by weight of particulate kaolin. A dust is obtained containing 3% by weight of the active ingredient.

VII. 30 parts by weight of compound no. 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 9 is intimately mixed with 10 parts by weight of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 27 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers.

Admixture with other fungicides frequently results in an increase in the fungicidal spectrum.

USE EXAMPLE

Action on Pyricularia oryzae (protective)

Leaves of pot-grown rice seedlings of the "Bahia" variety were sprayed to runoff with aqueous emulsions consisting (dry basis) of 80% of active ingredient and 20% of emulsifier, and inoculated 24 hours later with an aqueous spore suspension of Pyricularia oryzae. The plants were then set up in climatic cabinets at from 22° to 24° C. and a relative humidity of 95 to 99%. The extent of fungus spread was assessed after 6 days.

The results shown that active ingredients 2, 9 and 27, applied as 0.05 wt % spray liquors, have a good fungicidal action (95%).

We claim:

1. Substituted N-hydroxypyrazoles of the general formula I

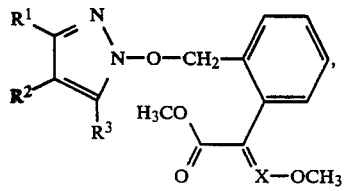

where
  $R^1$, $R^2$ and $R^3$ are identical or different and are hydrogen, $C_1$–$C_4$-alkyl, $C_1$–$C_2$-haloalkyl, $C_3$–$C_6$-cycloalkyl, $C_1$–$C_4$-alkoxycarbonyl, halogen, aryl or aryl-$C_1$–$C_4$-alkyl, the aromatic ring being unsubstituted or substituted by one or more of the following: $C_1$–$C_4$-alkyl, $C_3$–$C_6$-cycloalkyl, $C_1$–$C_2$-haloalkyl, $C_1$–$C_4$-alkoxy, halogen, cyano or nitro,
  or $R^2$ and $R^3$ form, with the pyrazole ring, an aromatic or aliphatic ring which is unsubstituted or substituted by $C_1$–$C_4$-alkyl,
  X is CH or N, and the acid addition salts and metal complexes thereof which are tolerated by plants.

2. A fungicide containing an inert carrier and a fungicidally effective amount of a substituted N-hydroxypyrazole of the general formula I

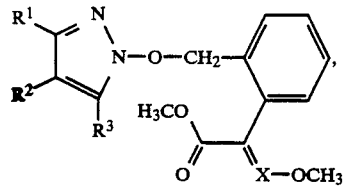

where
  $R^1$, $R^2$ and $R^3$ are identical or different and are hydrogen, $C_1$–$C_4$-alkyl, $C_1$–$C_2$-haloalkyl, $C_3$–$C_6$-cycloalkyl, $C_1$–$C_4$-alkoxycarbonyl, halogen, aryl or aryl-$C_1$–$C_4$-alkyl, the aromatic ring being unsubstituted or substituted by one or more of the following: $C_1$–$C_4$-alkyl, $C_3$–$C_6$-cycloalkyl, $C_1$–$C_2$-haloalkyl, $C_1$–$C_4$-alkoxy, halogen, cyano or nitro,
  or $R^2$ and $R^3$ form, with the pyrazole ring, an aromatic or aliphatic ring which is unsubstituted or substituted by $C_1$–$C_4$-alkyl,
  X is CH or N, or an acid addition salt or metal complex thereof tolerated by plants.

3. A process for combating fungi, wherein the fungi, or the materials, plants, seed or soil threatened by fungus attack are treated with a fungicidally effective amount of a substituted N-hydroxypyrazole of the general formula I

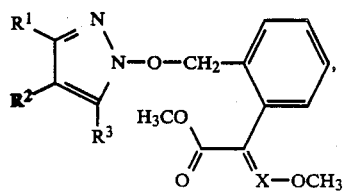

where
  $R^1$, $R^2$ and $R^3$ are identical or different and are hydrogen, $C_1$–$C_4$-alkyl, $C_1$–$C_2$-haloalkyl, $C_3$–$C_6$-cycloalkyl, $C_1$–$C_1$-alkoxycarbonyl, halogen, aryl or aryl-$C_1$–$C_4$-alkyl, the aromatic ring being unsubstituted or substituted by one or more of the following: $C_1$–$C_4$-alkyl, $C_3$–$C_6$-cycloalkyl, $C_1$–$C_2$-haloalkyl, $C_1$–$C_4$-alkoxy, halogen, cyano or nitro,
  or $R^2$ and $R^3$ form, with the pyrazole ring, an aromatic or aliphatic ring which is unsubstituted or substituted by $C_1$–$C_4$-alkyl,
  X is CH or N, or an acid addition salt or metal complex thereof tolerated by plants.

4. A compound of the formula I as set forth in claim 1, where $R^1$ and $R^3$ are each hydrogen, $R^2$ is chlorine and X is CH.

5. A compound of the formula I as set forth in claim 1, where $R^1$ and $R^3$ are each hydrogen, $R^2$ is chlorine and X is nitrogen.

6. A compound of the formula I as set forth in claim 1, where $R^1$ and $R^3$ are each methyl, $R^2$ is hydrogen and X is CH.

7. A compound of the formula I as set forth in claim 1, where $R^1$ and $R^3$ are each methyl, $R^2$ is hydrogen and X is nitrogen.

8. A compound of the formula I as set forth in claim 1, where $R^1$, $R^2$ and $R^3$ are each hydrogen and X is nitrogen.

* * * * *